United States Patent
Yu et al.

(10) Patent No.: US 6,766,189 B2
(45) Date of Patent: Jul. 20, 2004

(54) METHOD AND APPARATUS FOR PREDICTING ACUTE RESPONSE TO CARDIAC RESYNCHRONIZATION THERAPY

(75) Inventors: Yinghong Yu, Maplewood, MN (US); Jiang Ding, Maplewood, MN (US); Julio Spinelli, Shoreview, MN (US); Angelo Auricchio, Magdeburg (DE)

(73) Assignee: Cardiac Pacemakers, Inc., St. Paul, MN (US)

( * ) Notice: Subject to any disclaimer, the term of this patent is extended or adjusted under 35 U.S.C. 154(b) by 444 days.

(21) Appl. No.: 09/822,790

(22) Filed: Mar. 30, 2001

(65) Prior Publication Data

US 2002/0161307 A1 Oct. 31, 2002

(51) Int. Cl.[7] .................................. A61B 1/06
(52) U.S. Cl. ....................... 600/510; 600/509
(58) Field of Search ............... 607/9; 600/509, 600/510, 516

(56) References Cited

U.S. PATENT DOCUMENTS

| | | |
|---|---|---|
| 5,469,858 A | 11/1995 | Osborne |
| 5,694,942 A | 12/1997 | Escalona |
| 5,827,196 A | 10/1998 | Yeo et al. |
| 6,144,880 A | 11/2000 | Ding et al. |

*Primary Examiner*—Mark Bockelman
(74) *Attorney, Agent, or Firm*—Merchant & Gould

(57) ABSTRACT

A method and apparatus for predicting acute response to cardiac resynchronization therapy is disclosed. The method can comprise measuring a first interval during an intrinsic systolic cycle and measuring a second interval during a stimulated systolic cycle. The acute response can be predicted by comparing the percent change in duration between the first interval and the second interval against a predetermined threshold value. The first and second time intervals can be measured using, for example, a surface ECG or, alternatively, an intracardiac electrogram. In one embodiment, the first interval can be the duration of an intrinsic QRS complex measured during a non-stimulated systolic cycle. Similarly, the second interval can be the duration of a stimulated QRS complex measured during a stimulated systolic cycle.

39 Claims, 11 Drawing Sheets

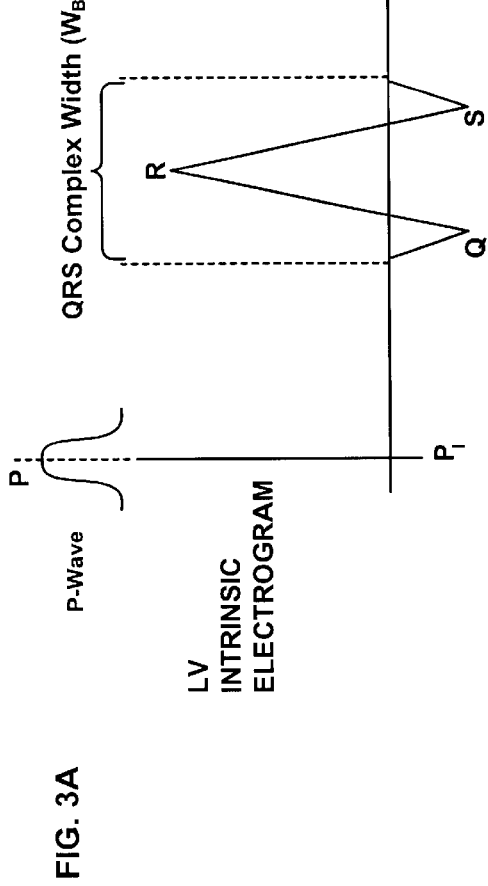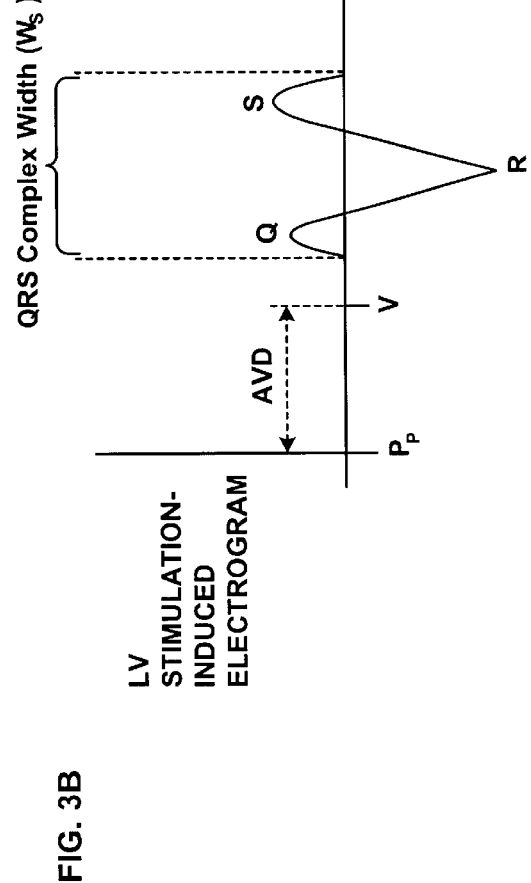

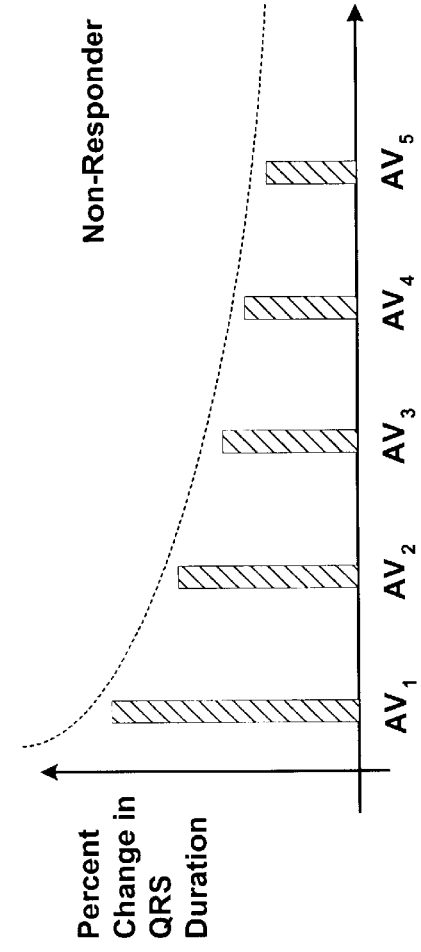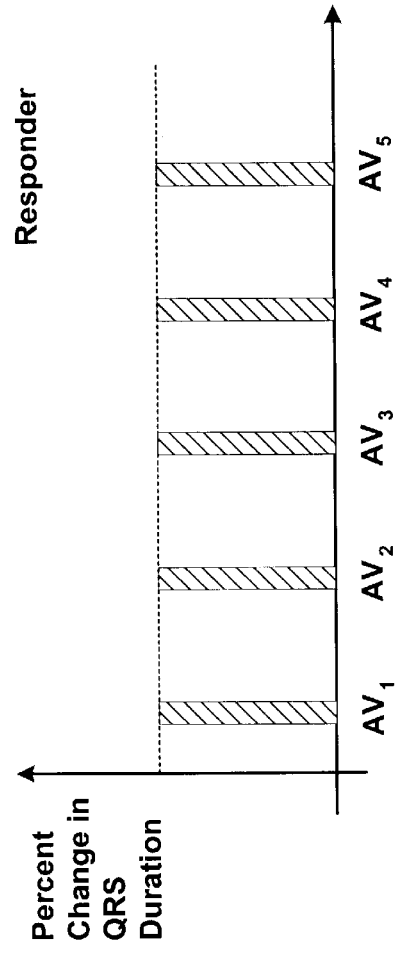
FIG. 7A
FIG. 7B

METHOD AND APPARATUS FOR PREDICTING ACUTE RESPONSE TO CARDIAC RESYNCHRONIZATION THERAPY

TECHNICAL FIELD

The present invention relates generally to a method and apparatus for administering stimulation therapy for heart disease and, more particularly, to a method and apparatus for predicting acute response to cardiac resynchronization therapy.

BACKGROUND

The heart is a muscular organ comprising multiple chambers that operate in concert to circulate blood throughout the body's circulatory system. As shown in FIG. 1, the heart 100 includes a right-side portion or pump 102 and a left-side portion or pump 104. The right-side portion 102 includes a right atrium 106 and a right ventricle 108. Similarly, the left-side portion 104 includes a left atrium 110 and a left ventricle 112. Oxygen-depleted blood returning to the heart 100 from the body collects in the right atrium 106. When the right atrium 106 fills, the oxygen-depleted blood passes into the right ventricle 108 where it can be pumped to the lungs (not shown) via the pulmonary arteries 117. Within the lungs, waste products (e.g., carbon dioxide) are removed from the blood and expelled from the body and oxygen is transferred to the blood. Oxygen-rich blood returning to the heart 100 from the lungs via the pulmonary veins (not shown) collects in the left atrium 110. The circuit between the right-side portion 102, the lungs, and the left atrium 110 is generally referred to as the pulmonary circulation. When the left atrium 110 fills, the oxygen-rich blood passes into the left ventricle 112 where it can be pumped throughout the entire body. In so doing, the heart 100 is able to supply oxygen to the body and facilitate the removal of waste products from the body.

To circulate blood throughout the body's circulatory system as described above, a beating heart performs a cardiac cycle that includes a systolic phase and a diastolic phase. During the systolic phase (e.g., systole), the ventricular muscle cells of the right and left ventricles 108, 112 contract to pump blood through the pulmonary circulation and throughout the body, respectively. Conversely, during the diastolic phase (e.g., diastole), the ventricular muscle cells of the right and left ventricles 108, 112 relax, during which the right and left atriums 106, 110 contract to force blood into the right and left ventricles 108, 112, respectively. Typically, the cardiac cycle occurs at a frequency between 60 and 100 cycles per minute and can vary depending on physical exertion and/or emotional stimuli, such as, pain or anger.

The contractions of the muscular walls of each chamber of the heart 100 are controlled by a complex conduction system that propagates electrical signals to the heart muscle tissue to effectuate the atrial and ventricular contractions necessary to circulate the blood. As shown in FIG. 2, the complex conduction system includes an atrial node 120 (e.g., the sinoatrial node) and a ventricular node 122 (e.g., the atrioventricular node). The sinoatrial node 120 initiates an electrical impulse that spreads through the muscle tissues of the right and left atriums 106, 110 and the atrioventricular node 122. As a result, the right and left atriums 106, 110 contract to pump blood into the right and left ventricles 108, 112 as discussed above. At the atrioventricular node 122, the electrical signal is momentarily delayed before propagating through the right and left ventricles 108, 112. Within the right and left ventricles 108, 112, the conduction system includes right and left bundles branches 126, 128 that extend from the atrioventricular node 122 via the Bundle of His 124. The electrical impulse spreads through the muscle tissues of the right and left ventricles 108, 112 via the right and left bundle branches 126, 128, respectively. As a result, the right and left ventricles 108, 112 contract to pump blood throughout the body as discussed above.

Normally, the muscular walls of each chamber of the heart 100 contract synchronously in a precise sequence to efficiently circulate the blood as described above. In particular, both the right and left atriums 106, 110 contract (e.g., atrial contractions) and relax synchronously. Shortly after the atrial contractions, both the right and left ventricles 108, 112 contract (e.g., ventricular contractions) and relax synchronously. Several disorders or arrhythmias of the heart can prevent the heart from operating normally, such as, blockage of the conduction system, heart disease (e.g., coronary artery disease), abnormal heart valve function, or heart failure.

Blockage in the conduction system can cause a slight or severe delay in the electrical impulses propagating through the atrioventricular node 122, causing inadequate ventricular relations and filling. In situations where the blockage in the ventricles (e.g., the right and left bundle branches 126, 128), the right and/or left ventricles 108, 112 can only be excited through slow muscle tissue conduction. As a result, the muscular walls of the affected ventricle (108 and/or 112) do not contract synchronously (e.g., asynchronous contraction), thereby, reducing the overall effectiveness of the heart 100 to pump oxygen-rich blood throughout the body. For example, asynchronous contraction of the left ventricular muscles can degrade the global contractility (e.g., the pumping power) of the left ventricle 112 which can be measured by the peak ventricular pressure change during systole (denoted as "LV+dp/dt"). A decrease in LV+dp/dt corresponds to a worsened pumping efficiency.

Similarly, heart valve disorders (e.g., valve regurgitation or valve stenosis) can interfere with the heart's 100 ability to pump blood, thereby, reducing stroke volume (i.e., aortic pulse pressure) and/or cardiac output.

Various medical procedures have been developed to address these and other heart disorders. In particular, cardiac resynchronization therapy ("CRT") can be used to improve the conduction pattern and sequence of the heart. CRT involves the use of an artificial electrical stimulator that is surgically implanted within the patient's body. Leads from the stimulator can be affixed at a desired location within the heart to effectuate synchronous atrial and/or ventricular contractions. Typically, the location of the leads (e.g., stimulation site) is selected based upon the severity and/or location of the blockage. Electrical stimulation signals can be delivered to resynchronize the heart, thereby, improving cardiac performance.

Despite these advantages, several shortcomings exist that limit the usefulness of CRT. For example, results from many clinical studies have shown that hemodynamic response to CRT typically varies from patient to patient, ranging from very positive (e.g., improvement) to substantially negative (e.g., deterioration). Additionally, hemodynamic response can also vary based upon the stimulation site used to apply CRT. Thus, in order to predict acute hemodynamic benefit from CRT, the patient typically must be screened prior to receiving the therapy and the actual stimulation site used to apply CRT should be validated for each patient. Existing methods that predict acute hemodynamic response to CRT are, therefore, patient specific. Furthermore, while some existing techniques and/or procedures can predict whether a specific patient will derive an acute hemodynamic benefit from CRT, they are unable to determine or validate that a specific stimulation site will produce a positive hemodynamic response from CRT.

Improvements in methods used to predict acute responses to CRT are, therefore, sought.

SUMMARY

In general terms, the present disclosure relates to a method and apparatus for administering stimulation therapy for heart disease. More particularly, the present disclosure relates to a method and apparatus for predicting acute response to cardiac resynchronization therapy. In one aspect of the disclosure, the method for predicting acute responses to cardiac resynchronization therapy can comprise measuring a first interval during an intrinsic systolic cycle; measuring a second interval during a stimulation-induced systolic cycle; and comparing the percent change in duration between the first interval and the second interval against a pre-determined threshold value.

The method can further comprise classifying a response type of at least one selected stimulation site according to the percent change in duration between the first interval and the second interval. In particular, the at least one selected stimulation site can be classified as responding if the percent change in duration between the first interval and the second interval is less than the pre-determined threshold value. Alternatively, the at least one selected stimulation site can be classified as non-responding if the percent change in duration between the first interval and the second interval is greater than or equal to the pre-determined threshold value.

In this aspect, the first interval can be an intrinsic QRS complex ($W_B$) measured during a non-stimulated systolic cycle. Similarly, the second interval can be a stimulated QRS complex ($W_S$) measured during a stimulation-induced systolic cycle. The intrinsic QRS complex can be evaluated as a function of more than one intrinsic systolic cycle. Furthermore, the intrinsic QRS complex can be evaluated as the average of the more than one intrinsic systolic cycle. The intrinsic systolic cycles used to evaluate the intrinsic QRS complex can be non-consecutive.

Further in this aspect, the stimulation-induced QRS complex can be evaluated as a function of more than one stimulated systolic cycles. Furthermore, the stimulation-induced QRS complex can be evaluated as the average of the more than one stimulation-induced systolic cycles. The stimulation-induced systolic cycles used to evaluate the stimulation-induced QRS complex can be non-consecutive. Moreover, the stimulation-induced QRS complex can be measured during ventricular stimulation at a short atrioventricular delay (AVD). The short AVD typically can be less than about one-half of an intrinsic atrioventricular interval (AV interval). More particularly, the short atrioventricular delay can be between the initiation of the AV interval (e.g., 0 AVD) to about one-fourth of the AV interval.

Still further in this aspect, the pre-determined threshold value can be between 10 and 25 percent of the change in duration between the intrinsic QRS complex ($W_B$) measured during a non-stimulated systolic cycle and the stimulation-induced QRS complex ($W_S$) measured during a stimulated systolic cycle. More particularly, the pre-determined threshold value is between 15 and 20 percent of the change in duration between the intrinsic QRS complex ($W_B$) measured during a non-stimulated systolic cycle and the stimulation-induced QRS complex ($W_S$) measured during a stimulated systolic cycle. Preferably, the pre-determined threshold value can be about 18 percent of the change in duration between the intrinsic QRS complex ($W_B$) measured during a non-stimulated systolic cycle and the stimulation-induced QRS complex ($W_S$) measured during a stimulated systolic cycle.

In yet another aspect, the present disclosure relates to a method for predicting acute responses to cardiac resynchronization therapy comprising: measuring an intrinsic QRS complex ($W_B$) during an intrinsic systolic cycle; measuring a stimulation-induced QRS complex ($W_S$) during a stimulated systolic cycle; the stimulation-induced QRS complex ($W_S$) being measured during ventricular stimulation at a short atrioventricular delay (AVD); and comparing the percent change in duration between the first interval and the second interval against a predetermined threshold value between 10 and 25 percent of the change in duration between the intrinsic QRS complex ($W_B$) and the stimulated QRS complex ($W_S$).

In still yet another aspect, the present disclosure relates to an apparatus for predicting acute responses to cardiac resynchronization therapy in accordance with the method described above. In this aspect, the apparatus comprises an electrocardiography device being configured to measure a first interval during an intrinsic systolic cycle and a second interval during a stimulated systolic cycle. The apparatus also comprises a programmer configured to measure the percent change in duration between the first interval and the second interval against a pre-determined threshold value.

In still yet another aspect, the present disclosure provides an alternative method for predicting acute responses to cardiac resynchronization therapy comprising: measuring a first interval during an intrinsic systolic cycle over more than one atrioventricular delay; measuring a second interval during a stimulated systolic cycle over each of the atrioventricular delays; determining the percent change in duration between the first interval and the second interval for each of the atrioventricular delays; and classifying an acute response type of at least one selected stimulation site according to variations in the percent change in duration between the first interval and the second interval across each of the atrioventricular delays. In this aspect, classifying an acute response type can include classifying the acute response type of the at least one selected stimulation site as responding if the percent change in duration between the first interval and the second interval is non-varying across each of the atrioventricular delays. Similarly, classifying an acute response type can include classifying the acute response type of the at least one selected stimulation site as non-responding if the percent change in duration between the first interval and the second interval is varying across each of the atrioventricular delays. An apparatus for predicting acute responses to cardiac resynchronization therapy using the method of this aspect is also disclosed.

BRIEF DESCRIPTION OF THE DRAWINGS

The invention may be more completely understood in consideration of the following detailed description of various embodiments of the invention in connection with the accompanying drawings, in which:

FIGS. 3A and 3B illustrate are graphs showing ventricular depolarization as a function of time;

FIGS. 7A and 7B are graphs illustrating a trend in change in atrioventricular delay as a function of variation in QRS complex duration for different response types;

Figure 1:
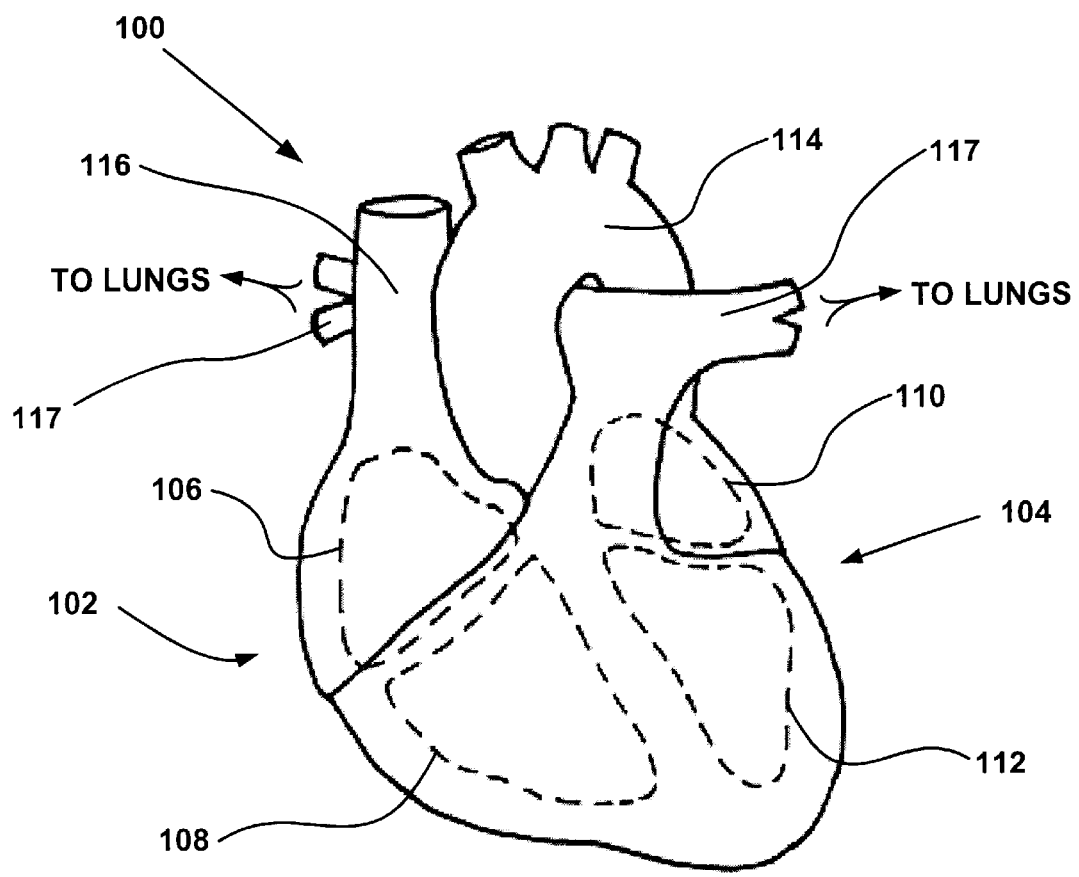
FIG. 1 is a diagram of a heart showing the various chambers of the heart.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

Various embodiments of the present invention will be described in detail with reference to the drawings, wherein like reference numerals represent like parts and assemblies throughout the several views. Reference to various embodiments does not limit the scope of the present invention, which is limited only by the scope of the claims attached hereto.

The following discussion is intended to provide a brief, general description of a suitable method for predicting a patient's acute response to cardiac resynchronization therapy ("CRT"). As will be described in greater detail below, the method of the present disclosure predicts a patient's acute response to CRT by measuring and/or comparing an intrinsic cardiac depolarization period against a cardiac depolarization period that is induced by electrical stimulation at a particular site or combination of sites. As will become apparent from the discussion below in connection with the various drawings, the method of present disclosure has particularized applicability when measuring and/or comparing intrinsic ventricular depolarization against stimulation-induced ventricular depolarization. However, those having ordinary skill in the art will readily appreciate that the method of the present disclosure can be implemented using any suitable cardiac depolarization periods, such as, the period between the peak of ventricular depolarization to the end of ventricular depolarization, or other cardiac depolarization periods.

In a preferred embodiment, the method of the present disclosure predicts a patient's acute response to CRT by evaluating the period of depolarization of the right and left ventricles 108, 112 (FIG. 1). The period of depolarization of the ventricles 108, 112 can be evaluated using, for example, an electrocardiogram ("ECG"). An ECG is generally a graphical depiction of the electrical depolarization or excitement of the heart 100 (FIG. 1) as electrical impulses spread through the heart 100 as described above. An exemplary ECG for an intrinsic systolic cycle is shown in FIG. 3A. Each portion of the ECG is typically given an alphabetic designation corresponding to a pre-determined period of electrical depolarization or excitement. For example, the portion of the ECG that represents atrial depolarization is commonly referred to as the P-wave. Similarly, the portion of the ECG that represents ventricular depolarization is commonly referred to as the QRS complex comprising, for example, a Q-wave, a R-wave, and a S-wave. Moreover, the portion of the ECG that represents ventricular recovery or repolarization is commonly referred to as the T-wave (not shown).

Figure 4A:
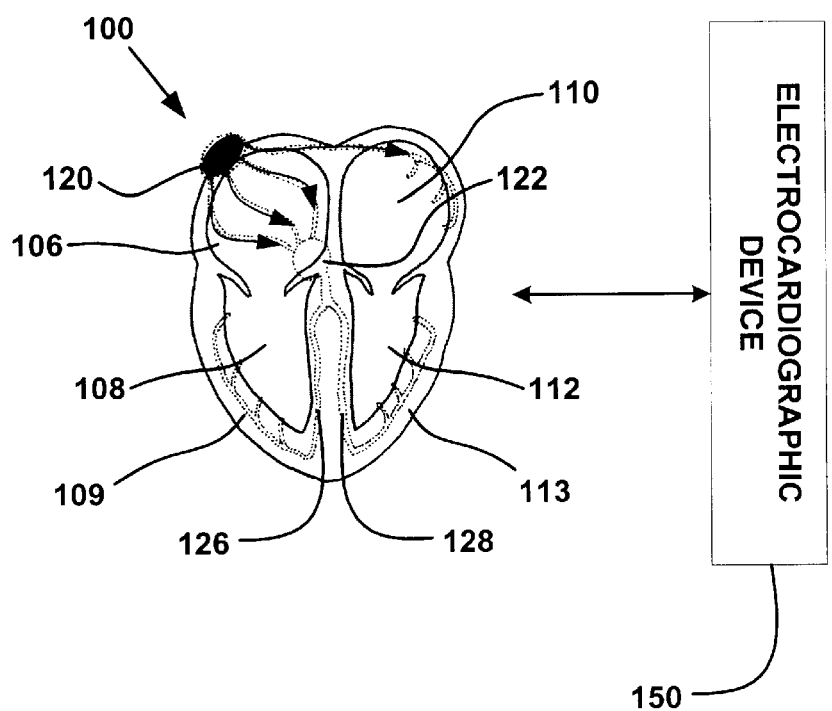
FIGS. 4A–4C are diagrams illustrating a heart and the electrical conduction system advancing through a normal cardiac cycle.
Figure 4B:
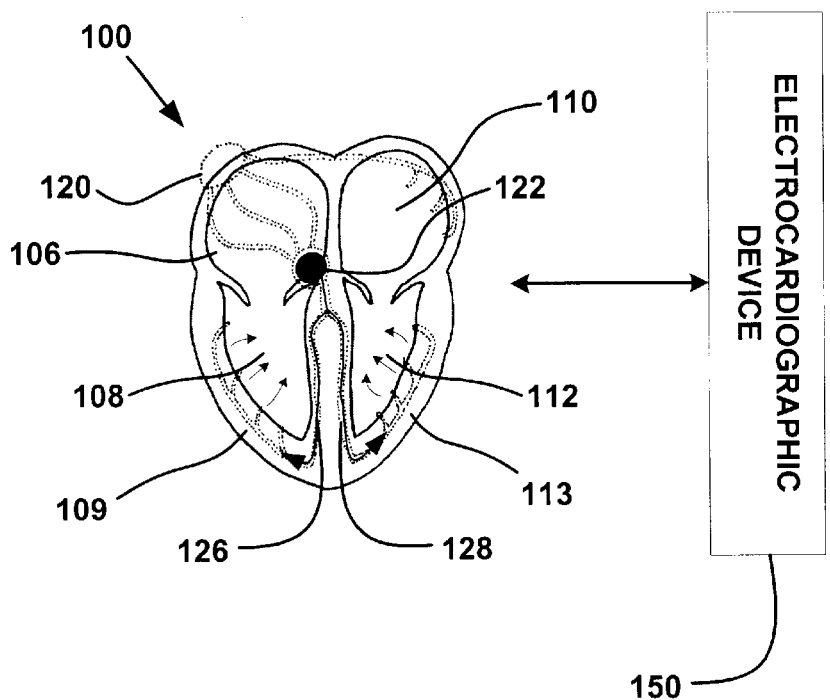
Figure 4C:
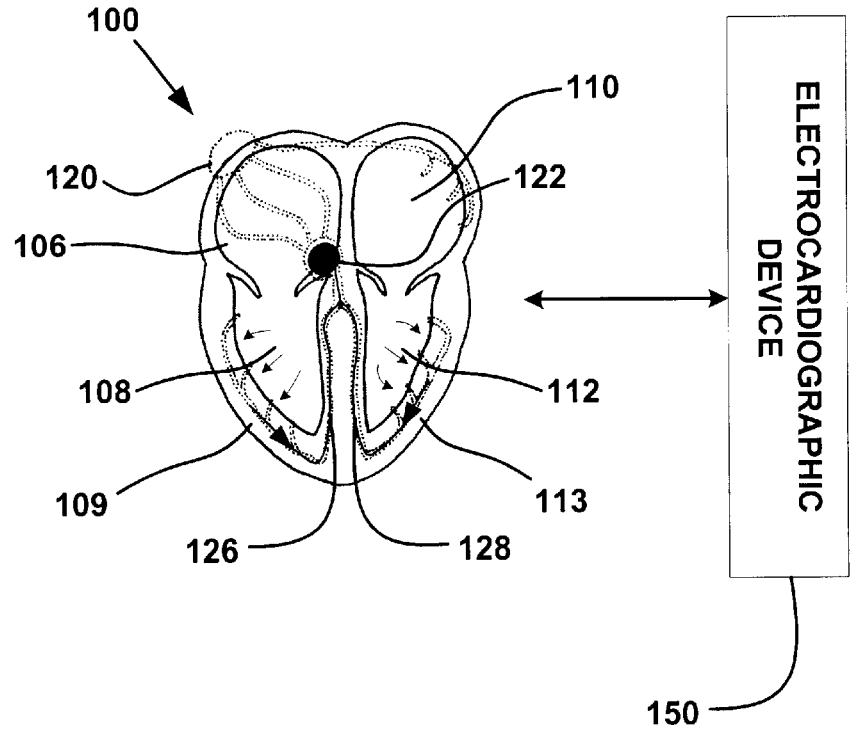

Each period of electrical depolarization or excitement represented on the ECG shown in FIG. 3A corresponds to a period of muscular activation within the heart 100 (FIG. 1). FIGS. 4A–4C are schematic illustrations depicting the various periods of muscular activation within the heart 100. Moreover, as shown in FIGS. 4A–4C, the ECG data can be monitored using any suitable electrocardiographic device 150, such as, a surface electrocardiographic device or an intracardiac device. FIG. 4A is a schematic illustration showing the period of atrial activation in response to electrical impulses initiated at the sinoatrial node 120 (corresponding to the P-wave portion of the ECG as discussed above). After electrical impulses spread from the sinoatrial node 120, the muscle tissues of the right and left atriums 106, 110 contract to pump blood into the right and left ventricles 108, 112, respectively. FIG. 4B is a schematic illustration showing the period of a ventricular depolarization in response to electrical impulses initiated at the atrioventricular node 122 and spread through the ventricles 108, 112 (corresponding to the QRS portion of the ECG as discussed above). After electrical impulses spread from the atrioventricular node 122, the muscle tissues of the right and left ventricles 108, 112 contract to pump blood to the lungs and throughout the body, respectively. FIG. 4C is a schematic illustration showing ventricular recovery or repolarization (corresponding to the T-wave portion of the ECG as discussed above). During ventricular repolarization, the membrane potential of the muscle cells reverse polarity and return to their resting state, thereby, causing the ventricles to relax.

An ECG of a patient's heart can be used to assess cardiac performance by validating the existence of cardiac abnormalities, such as, arrhythmias evinced by an abnormally fast heart rate (e.g., tachycardia), an abnormally slow heart rate (e.g., bradycardia), or a normal rate but the depolarization is abnormally propagated (e.g., ectopic, or conduction system defect). The existence of an arrhythmia typically indicates that the heart's rhythm initiation and/or conduction system is functioning abnormally. Since CRT can be used, among other applications, to treat abnormal electrical conduction, prior to treating a patient using CRT, it is preferable to evaluate whether the heart's 100 (FIG. 1) conduction system is normal or abnormal. In one possible embodiment, the heart's ventricular conduction system can be assessed by analyzing the duration of ventricular depolarization. In particular, the duration of ventricular depolarization in patients having a normal conduction system can generally be characterized as being less than or equal to about 80 milliseconds. By "normal," it is generally meant that ventricular depolarization within the heart 100 occurs synchronously as described above. Conversely, the duration of ventricular depolarization in patients having an abnormal conduction system can generally be characterized as being greater than about 80 milliseconds. By "abnormal," it is generally meant that ventricular depolarization within the heart 100 occurs asynchronously or in stages.

As discussed above, patients having an abnormal conduction system can potentially benefit from CRT. In particular, CRT can be used to deliver electrical stimulation to portions of the heart 100 (FIG. 1) to resynchronize the heart's activation, thereby, improving the efficiency of atrial and ventricular contractions necessary to circulate blood throughout the body. The amount of benefit derived from CRT, however, typically varies depending upon the severity of the abnormality of the heart's conduction system. Identification of patients that can benefit from CRT can be readily performed using, for example, the duration of ventricular depolarization (e.g., the width of the QRS complex). For example, if the duration of ventricular depolarization is greater than 120 milliseconds, it is generally believed that the patient can be considered as a possible candidate for CRT. If the duration of ventricular depolarization is greater than about 120 milliseconds, but less than about 150 milliseconds, it is generally believed that the patient can receive some benefit from CRT. Similarly, it is generally believed that a patient having a ventricular depolarization duration greater than about 150 milliseconds will receive significant benefit from CRT.

After the patient has been identified as being a possible candidate for CRT, the site for delivering the CRT stimuli (e.g., the electrical impulses) can be chosen. While many locations are contemplated, the stimulation site for delivering the CRT stimuli can be any suitable location within the coronary circulation system (e.g., the system of arteries and veins supplying/removing the heart 100 with oxygen-rich/oxygen-depleted blood), such as, a coronary artery or coronary vein. In a preferred embodiment, however, the stimulation site for delivering the CRT stimuli is within a coronary vein, such as, the Great Cardiac Vein. Moreover, the location of the CRT stimulation site is generally selected based upon the severity and/or location of the blockage within the conduction system.

Figure 2:
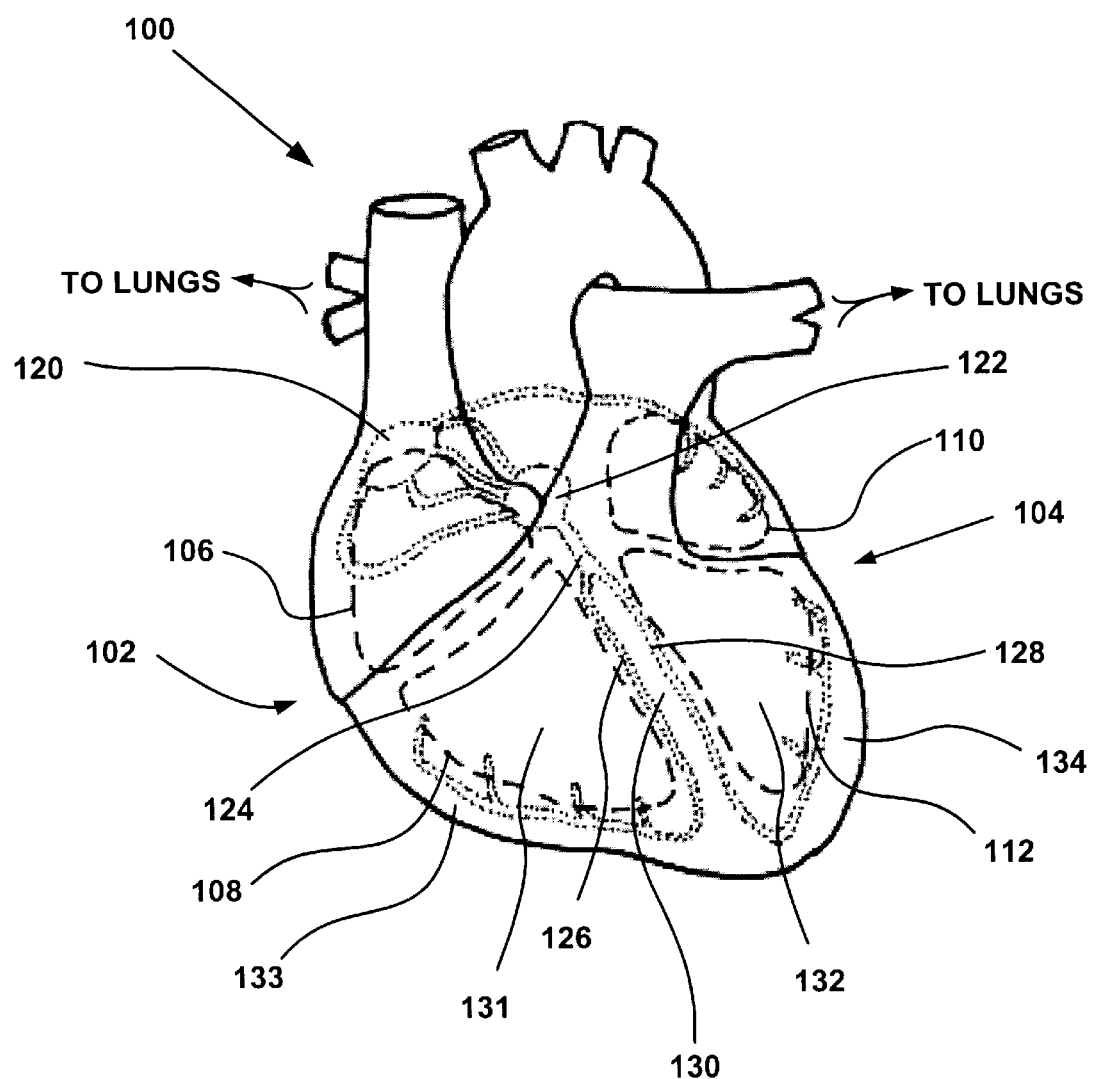
FIG. 2 is a diagram of a heart showing the various chambers and the electrical conduction system of the heart.

The CRT stimuli is preferably delivered at a location within a coronary blood vessel such that the stimulation-induced depolarization is synchronized with the intrinsic depolarization. For example, as shown in FIG. 2, with respect to the right ventricle 108, the CRT stimuli can be provided at the septum wall 130, a right ventricle anterior location 131, a right ventricle lateral wall location 133, or a right ventricle posterior location (not shown) opposite the anterior location 131. Similarly, with respect to the left ventricle 112, the CRT stimuli can be provided at the septum wall 130, a left ventricle anterior location 132, a left ventricle lateral wall location 134, or a left ventricle posterior location (not shown) opposite the anterior location 132. Thus, for example, if the conduction system is blocked within the Right Bundle Branch 126, the CRT stimuli can be provided at a lateral location, such as, within a lateral vein (not shown) at the lateral heart wall 133 of the right ventricle 108. Similarly, if the conduction system is blocked within the Left Bundle Branch 128, the CRT stimuli can be provided at a lateral location, such as, within a lateral vein (not shown) at the lateral heart wall 134 of the left ventricle 112. Alternatively, if the conduction system is blocked within both the Right Bundle Branch 126 and the Left Bundle Branch 128, the CRT stimuli can be provided at the septum wall 130, at the right ventricle lateral wall 133 and/or at the left ventricle lateral wall 134. In any event, one having ordinary skill in the art will readily appreciate that any suitable stimulation site or combinations of stimulation sites for delivering the CRT stimuli can be chosen such that the stimulation-induced depolarization is synchronized with the intrinsic depolarization, or with other CRT stimuli in case of multiple-site stimulation configurations.

Once a suitable stimulation site(s) has been identified, it is desirable to validate whether the selected stimulation site(s) will produce a positive hemodynamic response prior to completion of the procedure. To accomplish this, the present disclosure provides a method for predicting acute response to CRT for a selected stimulation site or combination of sites through assessment of a patient's conduction system. In particular, the method of the present disclosure predicts acute responses to CRT by comparing the percent change in duration between a first interval during an intrinsic systolic cycle and a second interval during a stimulated systolic cycle.

In one possible embodiment, the first interval can be the duration of a patient's intrinsic ventricular depolarization while the second interval can be the duration of the patient's ventricular depolarization induced by the delivery of the CRT stimuli at the selected stimulation site(s). As shown in FIG. 3A, the duration of the patient's intrinsic ventricular depolarization is the QRS complex width $W_B$ measured from normal intrinsic heart beats. Similarly, as shown in FIG. 3B, the duration of the patient's stimulation-induced ventricular depolarization is the QRS complex width $W_S$ measured after ventricular stimulation. Accordingly, the method of the present disclosure can predict acute responses to CRT by assessing the percent change in intrinsic QRS complex width (e.g., $W_B$) and stimulated QRS complex width (e.g., $W_S$). In one possible embodiment, the percent change in QRS complex width can be compared to a threshold value to predict whether a selected stimulation site or combination of sites will provide a positive hemodynamic response to CRT. The phrase "threshold value" generally refers to a pre-determined value that can be used to classify the selected stimulation site(s) as responding (e.g., a stimulation site(s) that is likely to provide a positive hemodynamic response to CRT) or non-responding (e.g., a stimulation site(s) that is unlikely to provide a positive hemodynamic response to CRT). The following expression can, therefore, be used to predict whether a given stimulation site or combination of sites can be used to provide a beneficial or positive hemodynamic response to CRT.

Stimulation Site:

$$\text{Responding } \frac{W_S - W_B}{W_S} < \text{THRESHOLD VALUE}$$

$$\text{Non-responding} \quad \frac{W_S - W_B}{W_S} \geq \text{THRESHOLD VALUE}$$

The QRS complex width can be measured using any suitable electrocardiographic device 150 (FIGS. 4A–4C). In one possible embodiment, the electrocardiographic device 150 is a surface ECG device. However, one having ordinary skill in the art will readily appreciate that the electrocardiographic device 150 can be an intracardiac device. In one possible embodiment, the QRS complex width can be taken as the maximum of a 12-lead ECG. The intrinsic QRS complex width $W_B$ can be evaluated as a function of one or more normal intrinsic systolic cycles (e.g., sinus beats). For example, in one possible embodiment, the intrinsic QRS complex width $W_B$ can be averaged over 16 normal instrinsic systolic cycles. In this embodiment, the systolic cycles used to measure the intrinsic QRS complex width $W_B$ can be selected consecutively. However, one having ordinary skill in the art will readily appreciate that the systolic cycles used to measure the intrinsic QRS complex width $W_B$ can be non-consecutive.

The stimulated QRS complex width $W_S$ is preferably measured during ventricular stimulation at a short atrioventricular delay ("AVD"). The atrioventricular delay is generally considered to be the length of time between an atrial sensed (or stimulated) event P and the delivery of a ventricular output pulse V (FIG. 3B). Further, by "short atrioventricular delay," it is generally meant that a ventricular stimulation will be delivered at some fraction of the overall intrinsic AV interval. For example, in one possible embodiment, the short AVD used to evaluate the stimulated QRS complex is typically less than about one-half (e.g., 0.5) of the intrinsic AV interval and, preferably, can range from an atrial sensed or stimulated event (e.g., the initiation of the AV interval or zero AVD) to about 0.25 of the intrinsic AV interval. In one embodiment of the present disclosure, the stimulated QRS complex width $W_S$ can be evaluated as a function of one or more stimulated systolic cycles. For example, the stimulated QRS complex width $W_S$ can be averaged over 16 stimulated systolic cycles between 0 AVD and 0.25 AVD.

Figure 5:
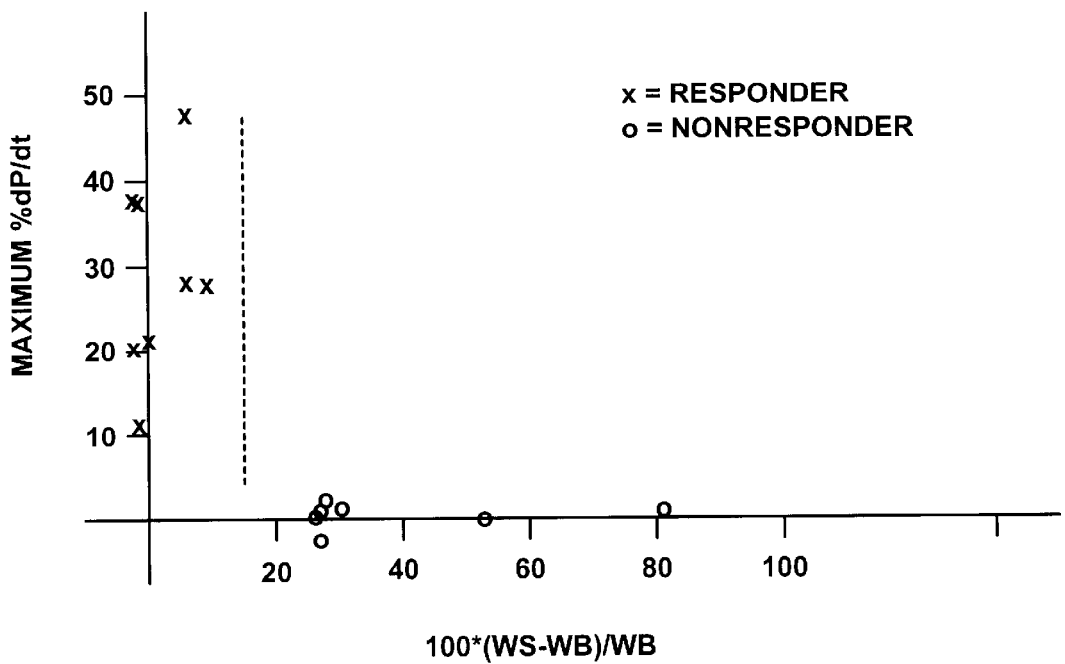
FIG. 5 is a graph illustrating maximum percentage improvement in left ventricular pressure change (LV+dp/dt) as a function of percent change in duration of ventricular depolarization for different response types.
Figure 6:
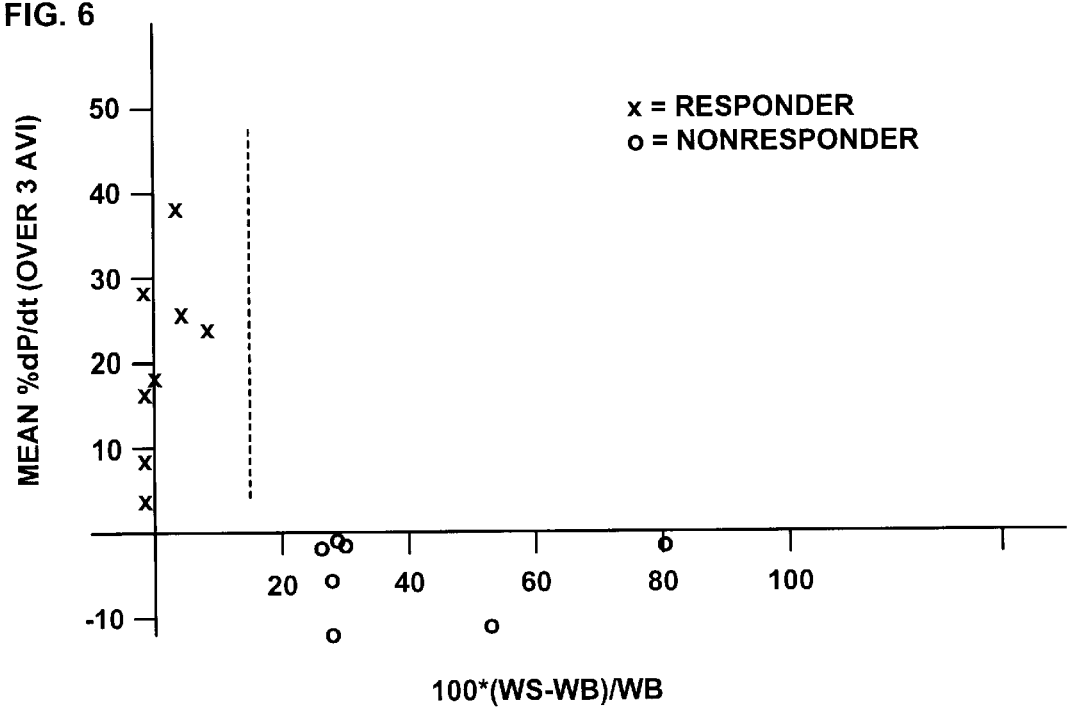
FIG. 6 is a graph illustrating mean percentage improvement in left ventricular pressure change (LV+dp/dt) as a function of percent change in duration of ventricular depolarization over more than one intrinsic AV intervals for different response types.

As discussed above, a threshold value can be used to classify selected stimulation sites as being responding (e.g., a stimulation site(s) that is likely to provide a positive hemodynamic response to CRT) or non-responding (e.g., a stimulation site(s) that is unlikely to provide a positive hemodynamic response to CRT). Clinical studies were undertaken to establish a suitable threshold value for classifying a given stimulation site as being either responding or non-responding. In particular, the threshold value can be determined from the relationship between percent change in ventricular pressure derivative (LV+dp/dt) and percent change in QRS complex width as discussed above. The results of the clinical evidence are shown in FIGS. 5 and 6. In the embodiment illustrated in FIG. 5, the percent change between stimulation and intrinsic baseline in the ventricular pressure derivative (LV+dp/dt) is measured at the left ventricle. Fifteen stimulation sites from twelve patients were evaluated during the clinical analysis summarized in FIG. 5. In this analysis, there were eight responding sites and seven non-responding sites. The stimulated QRS complex width $W_S$ for each site was averaged over 8 beats across two short AV delays (e.g., ¼th of the patient's instrinsic AV interval). Similarly, in the embodiment illustrated in FIG. 6, the mean percentage improvement in left ventricular pressure derivative (LV+dp/dt) is plotted against percent change in duration of ventricular depolarization (calculated in the same manner as the results shown in FIG. 5) for different response types. The dotted line in FIGS. 5 and 6 identifies a threshold value can be established to separate the responding stimulation sites and the non-responding stimulation sites. Using the results shown in FIGS. 5 and 6, a range for the threshold value can be estimated between about 10–25 percent, typically about 15–20 percent, and preferably about 18 percent of the change in QRS complex width. In so doing, the present disclosure provides a simple method that can be easily implemented to predict acute hemodynamic response to CRT for a given stimulation site or combination of sites.

FIGS. 7A and 7B illustrate an alternative embodiment for predicting acute response to CRT for selected stimulation sites. In particular, a patient's acute response to CRT can be predicted by analyzing the trends in more than one AV delay evaluated as a function of percent change in QRS width. Variations in the percent change in QRS width across multiple AV delay values typically indicates that the selected stimulation site(s) are non-responding. Accordingly, the patient will be unlikely to derive an acute hemodynamic benefit from CRT using the selected stimulation site(s). Conversely, small variations or no variations in QRS width across multiple AV delay values typically indicates that the selected stimulation site(s) are responding. Thus, for example, as shown in FIG. 7A, if the percent change in QRS complex width for a selected stimulation site(s) is variable as the AV delay is varied, the selected stimulation site(s) can be generally considered non-responding. As shown in FIG. 7B, if the percent change in QRS complex width for a selected stimulation site(s) is not varying as the AV delay is varied, the selected stimulation site(s) can be generally considered responding. While the graphs shown in FIGS. 7A and 7B illustrate the percent change in QRS width across five AV delays, one having ordinary skill in the art will readily appreciate that the number of AV delays can vary to include more AV delay values or less AV delay values.

The method of the present disclosure can be implemented using a CRT system comprising various devices and/or programmers, including implantable or external CRT devices and/or programmers, such as, a CRT tachy or brady system comprising, for example, a programmable pulse generator capable of transmitting electrical stimulation pulses. Accordingly, in addition to the above-described embodiments, the method of the present disclosure can be implemented as logical operations controlling a suitable CRT device and/or programmer. The logical operations of the present disclosure can be implemented: (1) as a sequence of computer implemented steps running on the CRT device and/or programmer; and (2) as interconnected machine modules within the CRT device and/or programmer. The implementation is a matter of choice dependant on the performance requirements of the CRT device and/or programmer implementing the method of the present disclosure and the components selected by or utilized by the users of the method. Accordingly, the logical operations making up the embodiments of the method of the present disclosure described herein can be referred to variously as operations, steps, subsystems, or modules.

Figure 10:
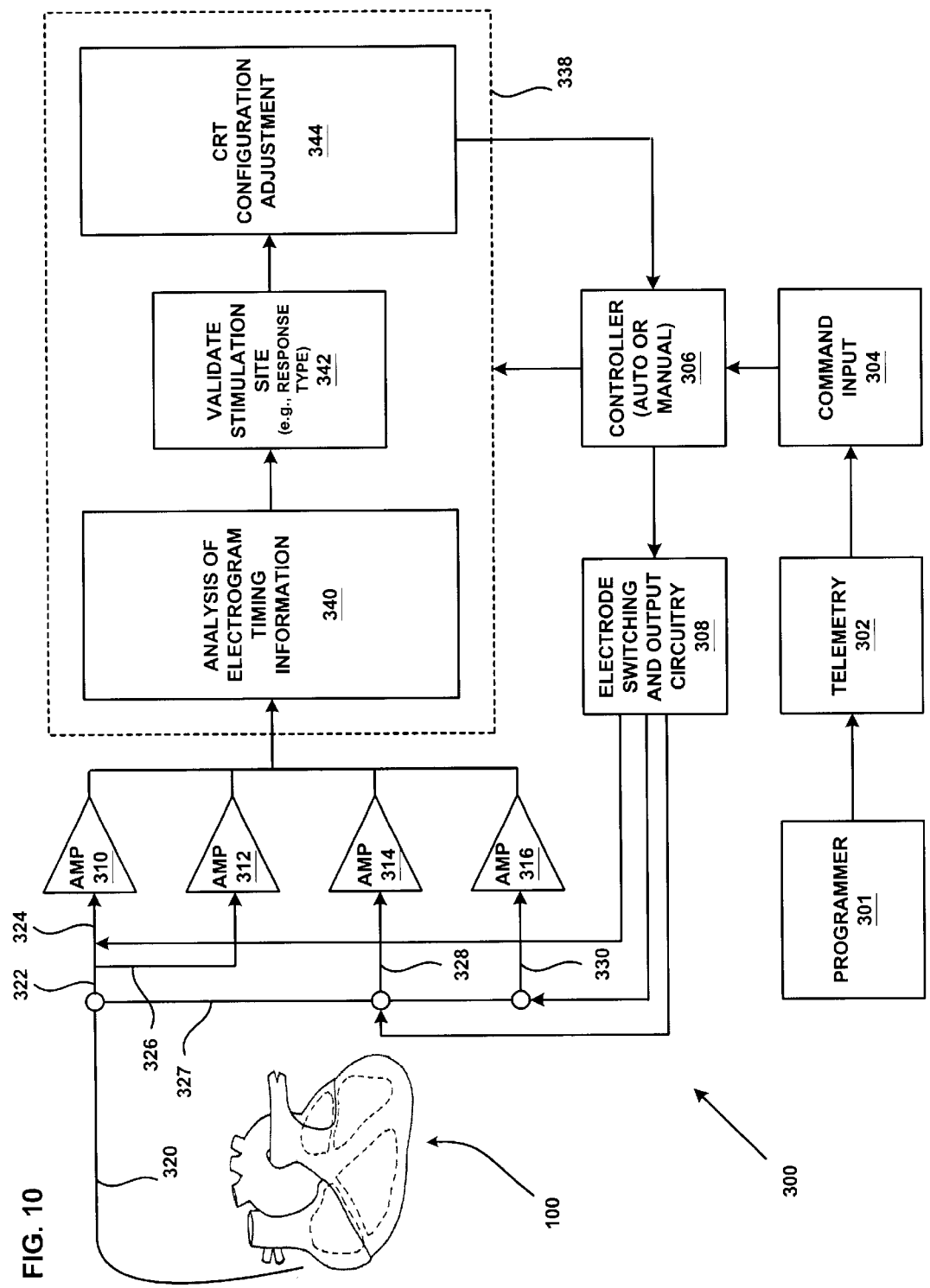
FIG. 10 illustrates one possible embodiment of a CRT system that can be used to implement the method of the present disclosure.

One possible embodiment of a CRT system 300 that can be used to implement the method of the present disclosure is illustrated in FIG. 10. As shown in FIG. 10, the CRT system 300 generally comprises a programming device 301 (e.g., pulse generator) that can be used to regulate stimulation pulses that are delivered to the heart 100. In one possible embodiment, the heart 100 is connected to various leads 320 having electrodes (not shown) and terminal pins (not shown) that can connect the heart 100 to the CRT system 300. The various leads 320 connecting the heart 100 to the CRT system 300 will be described in greater detail below.

The programmer 301 can regulate the stimulation pulses delivered to the heart 100 using, for example, a telemetry module 302. In one possible embodiment, the telemetry module 302 is unidirectional (e.g., capable of allowing the programmer 301 to receive data). However, in an alternative embodiment, the telemetry module 302 can be bi-directional (e.g., capable of allowing the programmer 301 to receive and/or send data). The command input module 304 is configured to interpret the data received from the programmer 301 such that the stimulation pulses can be accurately distributed according to predetermined criteria, such as, the specific requirements of the patient being treated. A controller 306 can be used to control the specific instructions regarding the stimulation pulses delivered to the heart 100. In one possible embodiment, the controller 306 can be controlled manually. In an alternative embodiment, however, the controller 306 can be controlled automatically using, for example, feedback received from an intrinsic signal analyzer 338. Moreover, one having ordinary skill in the art will readily appreciate that the controller 206 and the programmer 301 can be combined into a single unit. The instructions from the controller 306 are received by an electrode switching and output circuitry module 308 that delivers the stimulation pulses to the appropriate lead 320 within the heart 100.

As discussed above, the heart 100 is connected to the CRT system 300 using various lead 320. The various leads 320 are preferably configured to carry the CRT stimuli from the programmer 301 to the heart 100. Moreover, the various leads 320 can likewise operate in a demand mode, thereby, relaying intrinsic cardiac signals form the heart's 100 electrical conduction system back to one or more sense amplifiers 310, 312, 314, 316. In one possible embodiment, the various leads 320 comprise separate and distinct leads connecting the CRT system 300 to different portions of the heart 100. In particular, the various leads 320 can comprise a lead 322 connected to the right-side portion or pump 102 (FIG. 1) of the heart 100, including, for example, a right atrium lead 324 configured to operate with a right atrium amplifier 310 and a right ventricle lead 326 configured to operate with a right ventricle amplifier 312. Similarly, the various leads 320 can comprise a lead 327 connected to the left-side portion or pump 104 (FIG. 1) of the heart 100, including, for example, a first left ventricle lead 328 configured to operate with a first left ventricle amplifier 314 and a second left ventricle lead 330 configured to operate with a second left ventricle amplifier 316.

As discussed above, the various leads 320 connected to the heart 100 can relay intrinsic cardiac signals form the heart's 100 electrical conduction system back to the one or more sense amplifiers 310, 312, 314, 316. The intrinsic cardiac signals processed by the sense amplifiers 310, 312, 314, 316 can be processed by an intrinsic signal analyzer 338. The intrinsic signal analyzer 338 generally can comprise an analysis module 340 that is configured to analyze the electrocardiographic information gathered using, for example, an intracardiac electrogram. However, as discussed above, the electrocardiographic information can be gathered using a surface ECG. After analysis of the electrocardiographic information, the stimulation site(s) can be evaluated by a validation module 342 in accordance with the method described above. A configuration module 344 can be used to make adjustments to the CRT system 300 based upon whether the validation module 342 determines the selected stimulation site(s) to be responding or non-responding as described above.

Figure 8:
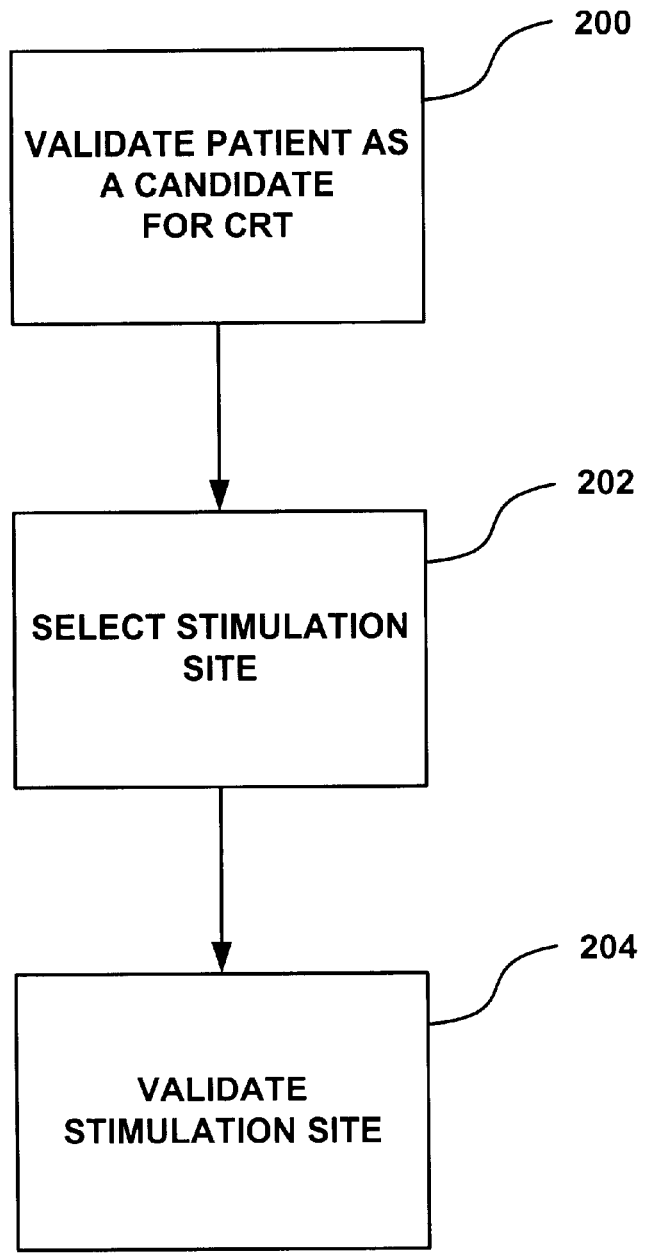
FIG. 8 is a high-level flow chart summarizing the logical operations of the method of predicting acute response to cardiac resynchronization therapy in accordance with the principles of the present disclosure.

Referring now to FIG. 8, a high-level flow chart summarizing the logical operations of the method of the present disclosure is shown. At operation 200, the patient is initially validated as a potential candidate for CRT. This can be accomplished, as discussed above, by comparing the patient's intrinsic QRS duration against predetermined criteria. At operation 202, the operator of the CRT device or programmer can select a suitable stimulation site within the patient's cardiac circulation system. Once the stimulation site is chosen, operation 204 validates the selected stimulation site as being either responding or non-responding as discussed above.

Figure 9:
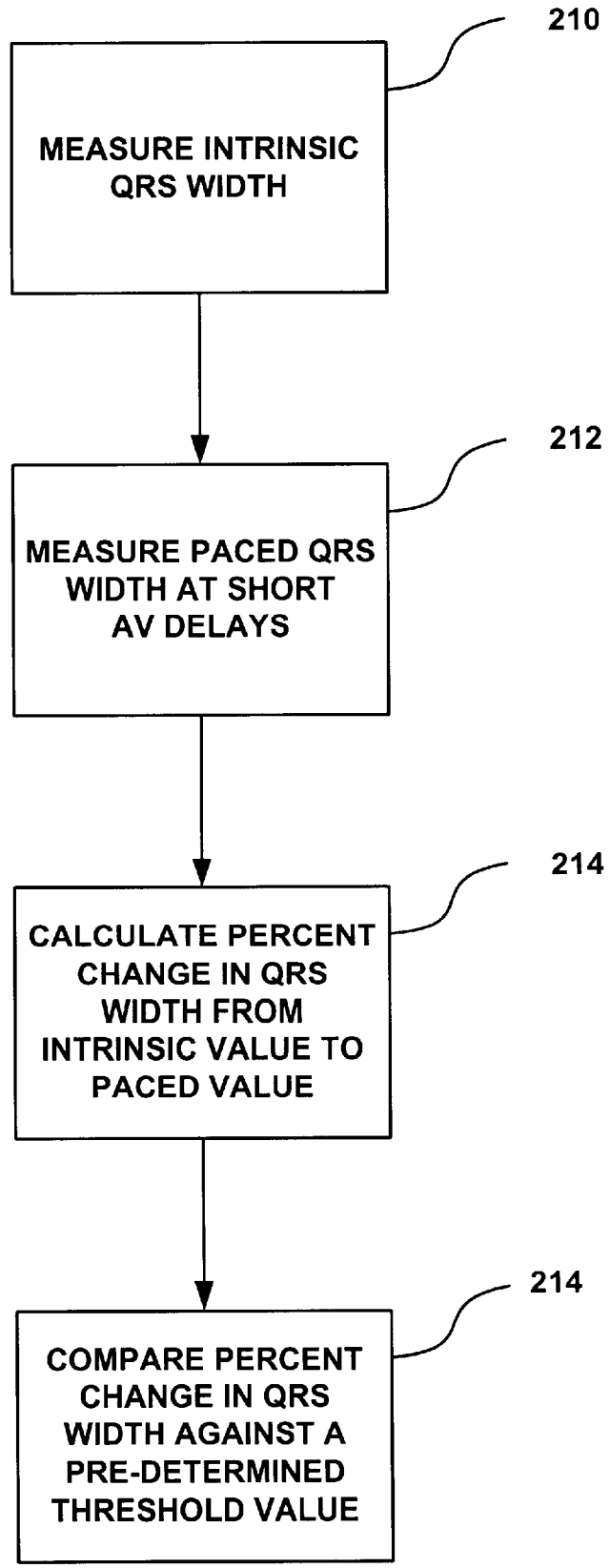
FIG. 9 is a detailed flow chart summarizing the logical operations used when validating a selected stimulation site in accordance with the principles of the present disclosure.

FIG. 9 provides a more detailed flow chart summarizing the logical operations followed when validating the selected stimulation site(s) and, therefore, predicting whether the patient will derive an acute hemodynamic benefit from CRT applied at the selected site(s). In one possible embodiment, validation of the selected stimulation site(s) is accomplished by first measuring the intrinsic QRS complex width $W_B$ at operation 210. As discussed above, the intrinsic QRS complex width $W_B$ can be measured using a surface ECG and evaluated as a function of one or more normal intrinsic systolic cycles (e.g., sinus beats). After measuring the intrinsic QRS complex width $W_B$, a stimulated QRS complex width $W_S$ can be measured at operation 212. The stimulated QRS complex width $W_S$ is preferably measured during ventricular stimulation at a short AV delay as discussed above. After measurement of the intrinsic QRS complex width $W_B$ and the stimulated QRS complex width $W_S$, the percent change in QRS complex width can be calculated at operation 214. The percent change in QRS complex width can be compared against a pre-determined threshold value at operation 216 to predict whether the selected stimulation site(s) are responding (e.g., a stimulation site(s) that is likely to provide a positive hemodynamic response to CRT) or non-responding (e.g., a stimulation site(s) that is unlikely to provide a positive hemodynamic response to CRT). Furthermore, the selected stimulation site(s) can be classified according to its response type.

Figure 7C:
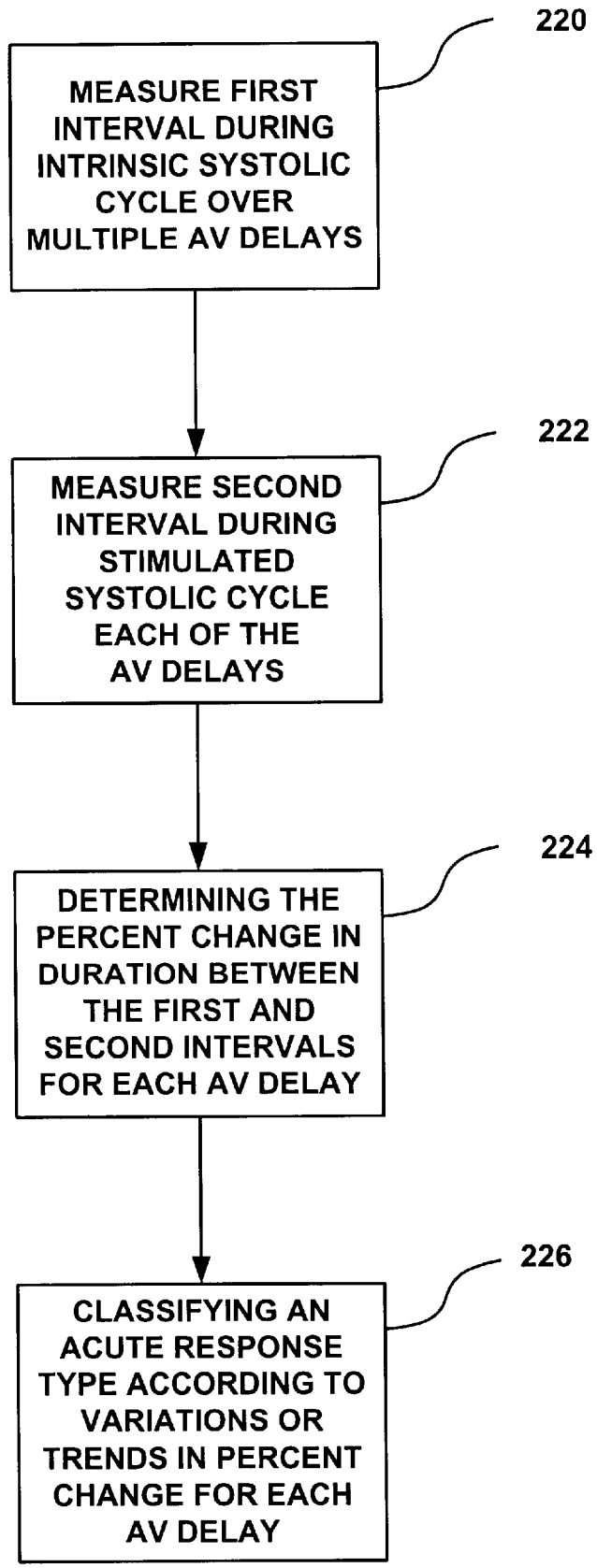
FIG. 7C is a flow chart summarizing the logical operations of method for predicting acute response to cardiac resynchronization therapy by analyzing the trends in change in atriventricular delay as a function of variation in QRS complex for different response types as shown in FIGS. 7A and 7B.

FIG. 7C is a flow chart summarizing the logical operations of the alternative embodiment for predicting acute response to CRT for selected stimulation sites described above in connection with FIGS. 7A and 7B. In this embodiment and as described above, the acute response to CRT can be predicted by analyzing the trends in more than one AV delay evaluated as a function of percent change in QRS width. As shown in FIG. 7C, at operation 220, a first interval during an intrinsic systolic cycle can be measured over more than one atrioventricular delays. At operation 222, a second interval during a stimulated systolic cycle can be measured over each of the atrioventricular delay. In one possible embodiment, the first interval can be an intrinsic QRS complex ($W_B$) measured during a non-stimulated systolic cycle and the second interval can be a stimulated QRS complex ($W_S$) measured during a stimulated systolic cycle. Once the first and second intervals are measured at operations 220 and 222, the percent change in duration between the first and second intervals for each AV delay can be determined at operation 224. The acute response type (e.g., responding or non-responding) can be classified according to analysis of the trends in percent change in duration between the first and second intervals at operation 226.

The various embodiments described above are provided by way of illustration only and should not be construed to limit the invention. Those skilled in the art will readily recognize the various modifications and changes which may be made to the present invention without strictly following the exemplary embodiments illustrated and described herein, and without departing from the true spirit and scope of the present invention, which is set forth in the following claims.

The claimed invention is:

1. A method for predicting acute responses to cardiac resynchronization therapy, the method comprising:
   (a) measuring a first interval during an intrinsic systolic cycle;
   (b) measuring a second interval during a stimulated systolic cycle; and
   (c) comparing the percent change in duration between the first interval and the second interval against a pre-determined threshold value.

2. The method according to claim 1 further comprising classifying an acute response type of at least one selected stimulation site according to the percent change in duration between the first interval and the second interval.

3. The method according to claim 2, wherein:
   (a) the at least one selected stimulation site is classified as responding if the percent change in duration between the first interval and the second interval is less than the pre-determined threshold value; and
   (b) the at least one selected stimulation site is classified as non-responding if the percent change in duration between the first interval and the second interval is greater than or equal to the pre-determined threshold value.

4. The method according to claim 1, wherein the pre-determined threshold value is between 10 and 25 percent of the change in duration between the first interval and the second interval.

5. The method according to claim 4, wherein the stimulated QRS complex ($W_S$) is evaluated as a function of more than one stimulated systolic cycles.

6. The method according to claim 5, wherein the stimulated QRS complex ($W_S$) is evaluated as the average of the more than one stimulated systolic cycles.

7. The method according to claim 5 wherein the more than one stimulated systolic cycles are non-consecutive.

8. The method according to claim 1, wherein each of the first and second intervals are measured using a surface electrocardiogram.

9. The method according to claim 1, wherein each of the first and second intervals are measured using an intracardiac electrocardiogram.

10. The method according to claim 1, wherein:
    (a) the first interval is an intrinsic QRS complex ($W_B$) measured during a non-stimulated systolic cycle; and
    (b) the second interval is a stimulated QRS complex ($W_S$) measured during a stimulated systolic cycle.

11. The method according to claim 10, wherein the intrinsic QRS complex ($W_B$) is evaluated as a function of more than one intrinsic systolic cycles.

12. The method according to claim 11, wherein the intrinsic QRS complex ($W_B$) is evaluated as the average of the more than one intrinsic systolic cycles.

13. The method according to claim 11, wherein the more than one intrinsic systolic cycles are non-consecutive.

14. The method according to claim 10, wherein the stimulated QRS complex ($W_S$) is measured during ventricular stimulation with a short atrioventricular delay (AVD).

15. The method according to claim 14, wherein the short atrioventricular delay (AVD) is less than about one-half of an intrinsic atrioventricular interval (AV interval).

16. The method according to claim 15, wherein the short atrioventricular delay (AVD) is between the initiation of the AV interval (AV interval) to about one-fourth of the AV interval.

17. The method according to claim 10, wherein the pre-determined threshold value is between 10 and 25 percent of the change in duration between the intrinsic QRS complex ($W_B$) measured during a non-stimulated systolic cycle and the stimulated QRS complex ($W_S$) measured during a stimulated systolic cycle.

18. The method according to claim 17, wherein the pre-determined threshold value is between 15 and 20 percent of the change in duration between the intrinsic QRS complex ($W_B$) measured during a non-stimulated systolic cycle and the stimulated QRS complex ($W_S$) measured during a stimulated systolic cycle.

19. The method according to claim 17, wherein the pre-determined threshold value is about 18 percent of the change in duration between the intrinsic QRS complex ($W_B$) measured during a non-stimulated systolic cycle and the stimulated QRS complex ($W_S$) measured during a stimulated systolic cycle.

20. A method for predicting acute responses to cardiac resynchronization therapy, the method comprising:
    (a) measuring an intrinsic QRS complex ($W_B$) during an intrinsic systolic cycle as a first interval;
    (b) measuring a stimulated QRS complex ($W_S$) during a stimulated systolic cycle as a second interval; the stimulated QRS complex ($W_S$) being measured during ventricular stimulation at a short atrioventricular delay (AVD);
    (c) comparing the percent change in duration between the first interval and the second interval against a pre-determined threshold value between 10 and 25 percent of the change in duration between the first interval and the second interval; and
    (d) classifying an acute response type of at least one selected stimulation site according to the percent change in duration between the first interval and the second interval.

21. The method according to claim 20, wherein:
    (a) the at least one selected stimulation site is classified as responding if the percent change in duration between the first interval and the second interval is less than the pre-determined threshold value; and
    (b) the at least one selected stimulation site is classified as non-responding if the percent change in duration between the first interval and the second interval is greater than or equal to the pre-determined threshold value.

22. The method according to claim 20, wherein each of the first and second intervals are measured using a surface electrocardiogram.

23. The method according to claim 20, wherein each of the first and second intervals are measured using an intracardiac electrocardiogram.

24. The method according to claim 20, wherein the intrinsic QRS complex ($W_B$) is evaluated as a function of more than one intrinsic systolic cycles.

25. The method according to claim 24, wherein the intrinsic QRS complex ($W_B$) is evaluated as the average of the more than one intrinsic systolic cycles.

26. The method according to claim 24, wherein the more than one intrinsic systolic cycles are non-consecutive.

27. The method according to claim 20, wherein the stimulated QRS complex ($W_S$) is evaluated as a function of more than one stimulated systolic cycles.

28. The method according to claim 27, wherein the stimulated QRS complex ($W_S$) is evaluated as the average of the more than one stimulated systolic cycles.

29. The method according to claim 27, wherein the more than one stimulated systolic cycles are non-consecutive.

30. The method according to claim 20, wherein the short atrioventricular delay (AVD) is less than about one-half of an intrinsic atrioventricular interval (AV interval).

31. The method according to claim 30, wherein the short atrioventricular delay (AVD) is between the initiation of the AV interval (AV interval) to about one-fourth of the AV interval.

32. The method according to claim 20, wherein the pre-determined threshold value is between 15 and 20 percent of the change in duration between the intrinsic QRS complex ($W_B$) measured during a non-stimulated systolic cycle and the stimulated QRS complex ($W_S$) measured during a stimulated systolic cycle.

33. The method according to claim 32, wherein the pre-determined threshold value is about 18 percent of the change in duration between the intrinsic QRS complex ($W_B$) measured during a non-stimulated systolic cycle and the stimulated QRS complex ($W_S$) measured during a stimulated systolic cycle.

34. A method for predicting acute responses to cardiac resynchronization therapy, the method comprising:
   (a) measuring a first interval during an intrinsic systolic cycle over more than one atrioventricular delay;
   (b) measuring a second interval during a stimulated systolic cycle over each of the atrioventricular delays; and
   (c) determining the percent change in duration between the first interval and the second interval for each of the atrioventricular delays; and
   (d) classifying an acute response type of at least one selected stimulation site according to variations in the percent change in duration between the first interval and the second interval across each of the atrioventricular delays.

35. The method according to claim 34, wherein classifying an acute response type includes:
   (a) classifying the acute response type of the at least one selected stimulation site as responding if the percent change in duration between the first interval and the second interval is non-varying across each of the atrioventricular delays; and
   (b) classifying the acute response type of the at least one selected stimulation site as non-responding if the percent change in duration between the first interval and the second interval is varying across each of the atrioventricular delays.

36. The method according to claim 34, wherein each of the first and second intervals are measured using a surface electrocardiogram.

37. The method according to claim 34, wherein each of the first and second intervals are measured using an intracardiac electrocardiogram.

38. The method according to claim 34, wherein:
   (a) the first interval is an intrinsic QRS complex ($W_B$) measured during a non-stimulated systolic cycle; and
   (b) the second interval is a stimulated QRS complex ($W_S$) measured during a stimulated systolic cycle.

39. The method according to claim 38, wherein classifying an acute response type includes:
   (a) classifying the acute response type of the at least one selected stimulation site as responding if the percent change in duration between the intrinsic QRS complex ($W_B$) and the stimulated QRS complex ($W_S$) is non-varying across each of the atrioventricular delays; and
   (b) classifying the acute response type of the at least one selected stimulation site as non-responding if the percent change in duration between the intrinsic QRS complex ($W_B$) and the stimulated QRS complex ($W_S$) is varying across each of the atrioventricular delays.

* * * * *